United States Patent [19]

Pauls

[11] 4,195,532
[45] Apr. 1, 1980

[54] SKI STIFFNESS AND CAMBER INDICATOR

[76] Inventor: Edward A. Pauls, Rte. 1, Box 615P, Excelsior, Minn. 55331

[21] Appl. No.: 921,275

[22] Filed: Jul. 3, 1978

[51] Int. Cl.² .............................................. G01N 3/20
[52] U.S. Cl. ...................................................... 73/849
[58] Field of Search ...................... 73/849, 141 R, 818, 73/161, 141 A; 100/99; 280/601, 602

[56] References Cited

U.S. PATENT DOCUMENTS

| | | | |
|---|---|---|---|
| 2,082,364 | 6/1937 | Store | 73/818 X |
| 2,222,079 | 11/1940 | Larson | |
| 2,224,248 | 12/1940 | Blum et al. | 100/99 UX |
| 2,628,496 | 2/1953 | Wick | 73/818 |
| 2,691,886 | 10/1954 | Cole | |
| 2,795,953 | 6/1957 | Makowsky | 73/172 |
| 3,178,937 | 4/1965 | Bradley | 73/141 R |
| 3,400,573 | 9/1968 | Matter | |
| 3,964,300 | 6/1976 | Howe | 73/849 |

*Primary Examiner*—Jerry W. Myracle
*Attorney, Agent, or Firm*—Kinney, Lange, Braddock, Westman and Fairbairn

[57] ABSTRACT

A ski stiffness indicator comprising a type of a C clamp which receives a pair of skis placed bottom to bottom, and which can be used to force the middle portions of the skis together. The force required for urging the portions of the skis together is registered on a gage, and the flexing of the skis under a selected load indicates the stiffness of the skis, and thus indicates the relative flex to select skis for varying conditions. Also, the load required to make the skis touch along their length indicates the ski stiffness.

9 Claims, 3 Drawing Figures

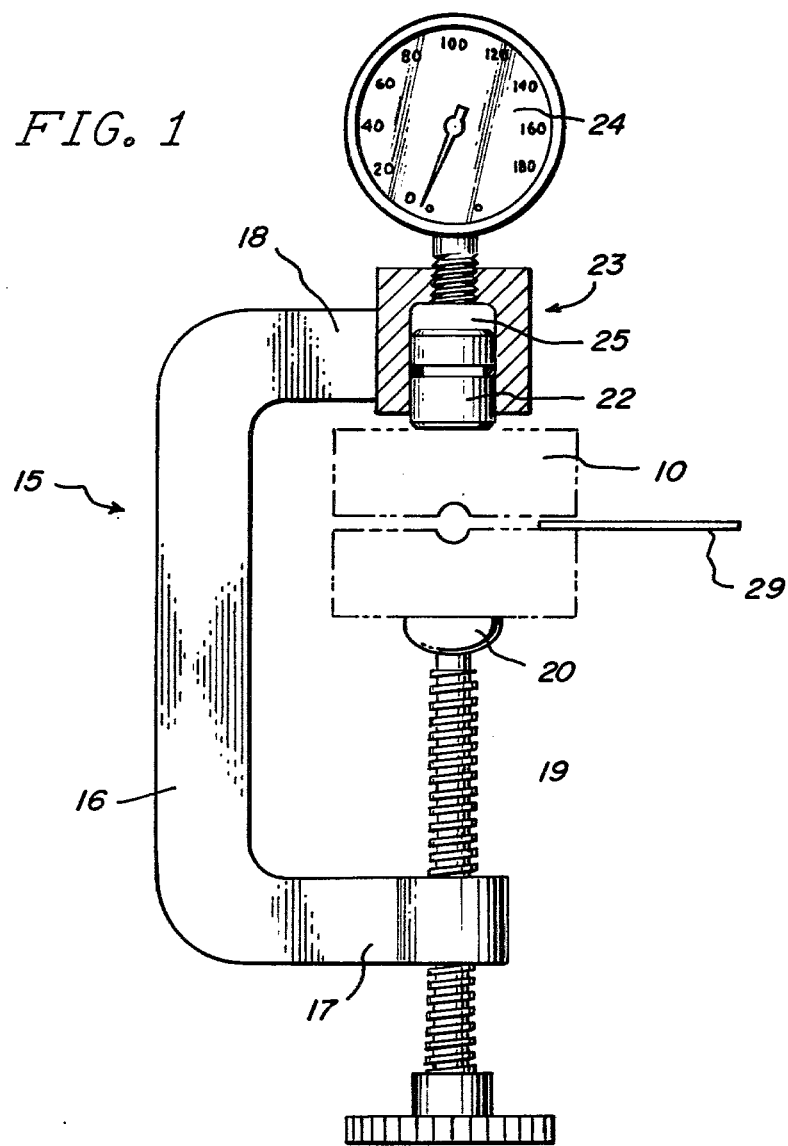
FIG. 1
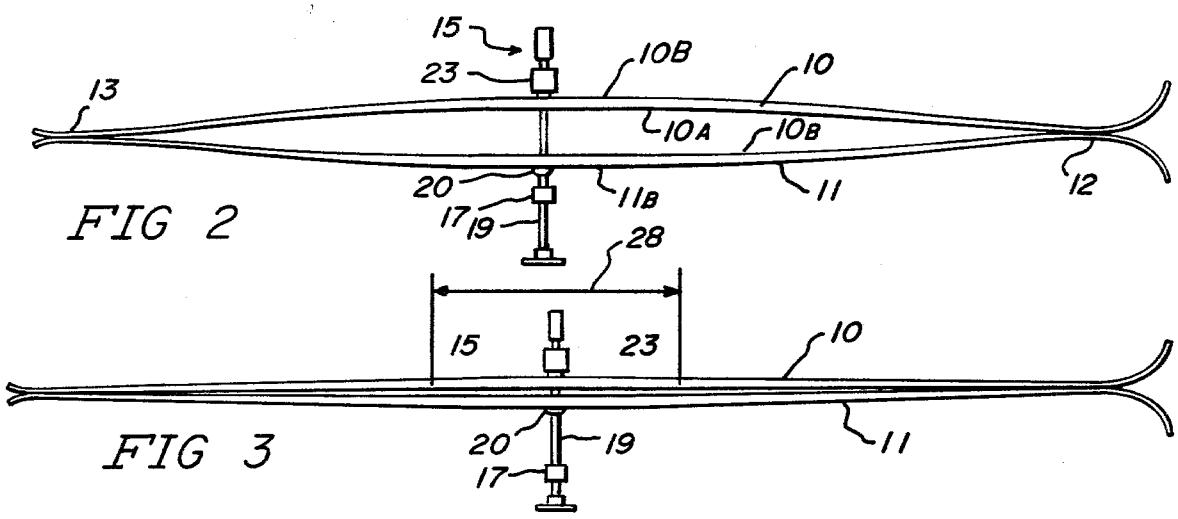
FIG 2
FIG 3

4,195,532

SKI STIFFNESS AND CAMBER INDICATOR

BACKGROUND OF THE INVENTION

1. Field of the Invention

The present invention relates to testing devices and methods for testing ski stiffness.

2. Prior Art

In the prior art the determination of ski stiffness has been desirable for some time. One method has comprised the placing of the ski with the bottom side down on a flat surface, and then having a person first stand on one of the skis while a business card or some type of thickness gage is placed under the ski, and the amount of movement of the card longitudinally along the ski (between the floor and the ski) from the center where the person's foot is resting will determine whether or not the ski camber and stiffness is proper. If the person stands on both skis so that the weight of the person is half on each of the skis in a pair, the test card will again be moved to determine whether or not a sufficient length of clearance is present.

Various testers for measuring the stress of materials and the like have also been advanced. For example U.S. Pat. No. 2,691,886 discloses a device for measuring the stress of gasket material, which includes a compression shoe adapted to engage a plunger which compresses the gasket material and the pressure is readable on a pressure gage.

U.S. Pat. No. 2,222,079 is a tester for vessel liners which includes a C clamp type of device and a force measuring member. However, this device does not contemplate the use for stiffness testing of skis. Additional patents which illustrate the state of the art include U.S. Pat. No.'s 2,795,953 and 3,400,573.

SUMMARY OF THE INVENTION

The present invention relates to an apparatus for quickly testing the relative stiffness of a pair of skis by clamping the skis together, bottom to bottom, and applying a desired amount of force on the skis and measuring the length of the gap. Also, another test is to push the skis together to a desired spacing or with the skis touching and determining the force required to do so. At that time, the skis also may be visually compared for evenness or uniformity of stiffness and for location of the gap.

The apparatus utilized is a C clamp type of device which includes a movable support member that will rest against a pair of skis placed bottom to bottom. A pressure reading plunger or gage is placed on the stationary back-up member of the C clamp. A pair of skis placed bottom to bottom are positioned within the C clamp between the support member and the plunger. The movable member is operated to compress the skis a desired amount. The clamp can be closed until the amount of force desired is applied, or the skis can be compressed until they just touch, and the force that is necessary can be noted. The stiffness of the skis can be determined, and also the match between the skis can be checked.

In the method of determining the stiffness of skis, a pair of skis are placed bottom to bottom in the loading device, and a load equal to approximately one-half of the person's weight is applied at about the location of the ball of the foot of a user. The load tends to compress the skis or remove the camber from the skis at the center portions. The spacing may be checked by the use of a thin card, and the total length of spacing between the skis can be determined. This measurement aids in determining the suitability of the ski for use.

The device is portable and can be carried to the ski slopes. Particularly in the case of cross country skiing meets and the like, the skis can be checked for camber and also can be checked for uniformity between the skis in a pair by observing the straightness and relative deflection of each of the skis when they are contacting.

The camber of a ski spreads the pressure of the weight of a skier on the snow over the entire length of the ski, and thus light camber would be used by a lighter person, and a stiff ski would be used by a heavier person even though the skis may both be the same length. It has been difficult for the skiers to determine the flexing or stiffness of a ski on the slopes, and to thus select the proper ski for the person's weight and the type of skiing. Further, snow conditions have some definite bearing on the stiffness of the ski that is more desirable.

With the present device and method, the skis can be tested simply and at skiing locations if desired in order to select skis to suit the existing snow conditions as well as the individual person that is using the skis.

BRIEF DESCRIPTION OF THE DRAWINGS

FIG. 1 is a side elevational view of a ski tester made according to the present invention illustrating a pair of skis in position to be tested;

FIG. 2 is a sectional view taken as on line 2—2 in FIG. 1; and

FIG. 3 is a further view showing the processes of the present invention being carried out.

DESCRIPTION OF THE PREFERRED EMBODIMENT

In FIG. 1, a first ski 10 and a second ski 11 are placed with their bottom surfaces 10A and 11A facing each other. These skis as shown have center portions 10B and 11B which are cambered or in other words would be spaced from a plane that would lie along the contact points of the skis.

When unloaded as shown schematically in FIG. 2, the skis contact each other at the point 12 adjacent the forward ends, and at 13 adjacent the tail. These skis with their bottom surfaces facing each other are then placed into a stiffness testing apparatus indicated generally at 15. Referring to FIG. 1 this apparatus is shown in greater detail. The apparatus 15 includes a frame 16, which is generally similar to the C clamp construction, and has a base 17 and a sensing leg 18, which are positioned to generally extend parallel to each other from the main portion of a clamp. The base 17 threadably mounts a clamping or adjusting screw 19 which has a support portion or member 20 at its end.

The support portion 20 forms an adequate surface for supporting the ski 11 as shown, and the ski 10 is supported against a piston or plunger 22 of a hydraulic pressure gage assembly 23, which has a read-out gage 24 leading to the interior portion of a cylinder shown at 25, in which the plunger 22 is mounted. The pressure on the interior of the cylinder 25 is registered on the gage 24, and this gage can be calibrated to read directly in pounds of force. If a 1⅛ inch diameter piston 22 is used, the pounds per square inch reading is substantially the same as the actual pounds of force because the piston is approximately one square inch in area.

Thus, all that has to be done with the device is to place the skis bottom to bottom as shown, unthread the screw 19 to a certain opening necessary to receive the skis between the members 20 and 22. The load will be applied approximately at the same location as the ball of a skier's foot. The screw 19 is threaded to compress the skis until the desired load is indicated on gage 24, or until such time as the spacing is as desired, and the load then can be read directly from the gage 24.

If desired, the distance between the points of contact of the skis can be measured relative to the loading device to determine the length of spacing of the skis and in this way get another determination of the actual stiffness of the ski in relation to its contact with the snow. Note that the arrow 28 represents this spacing in FIG. 3. A thin card or gage 29 may be inserted in the ski gap and slid to the contact point at both front and rear, and the distance measured.

The unit of course is quite easily made, and it can be utilized in most places because of its portability. It should be noted that the housing 23 is fixed to the member 28 so that the reaction from the load is carried by the clamp members 16 between members 17 and 18.

In normal use a force equal to half the skier's weight is applied. This will correspond to the situation in which a skier stands with his weight distributed equally on both skis. Cross country racing skis are usually of such stiffness that with this pressure applied, there will still be a small gap between the ski bottoms near the center of the skis.

The length and location of the gap between skis can be noted. Most skiers prefer a length of about 18 inches. Some skiers may, from experience, prefer a slightly longer or shorter gap length, but a gap length of shorter than 12 inches or longer than 24 inches will usually mean that the skis are unsuited for the skier.

The gap location is also important. It should be centered near the skier's ball of foot location on the ski. If the gap is centered far forward or aft of this location, the ski design or manufacturing process was faulty. If the gap center is displaced plus or minus two inches it is generally satisfactory.

A further test is to apply a pressure with the ski tester such that the gap between the skis just closes completely. This pressure will be called the closing pressure. Most ski racers prefer skis with a closing pressure of approximately 0.7 times their weight. Somewhat softer skis sometimes work better in softer than usual snow conditions.

With the gap between the skis completely closed, a check for manufacturing defects should be made. By sighting down the length of the bottom edges of the line, formed by the bottom edges of the two skis, straightness can be checked. Curvature or waviness of this line means that the skis are of unequal stiffness and therefore less desirable. Gaps between the ski bottoms forward or aft of the clamp-closed center of the ski also indicate a poorer quality ski.

Touring (non-racing) cross country skis can also be tested for closing pressure. They should close at a pressure approximately equal to half the skier's weight.

Cross country racing skis are now waxed with a gripping wax for only a short distance (about 18 inches) along the center of the ski. The skis are of a flex stiff enough to remove most of the skier's weight from this portion of the ski when the skier has his weight equally distributed between both skis. This provides better speed down hills because the gripping wax does not slide nearly as well as the "speed" wax applied to both ends of the ski. When the skier "kicks" (pushes himself forward) with one leg, his weight is all on this one ski and the gripping wax is brought in solid contact with the snow for good grip.

To achieve this ideal situation of skiing with the short gripping section of the ski coming in contact with the snow only at the desired time, a ski must be selected to have proper flex stiffness. The described method accurately tests the stiffness and stiffness distribution of the skis to aid in selection by observing and determining the parameters of gap between the bottom to bottom skis and the force compressing the skis.

What is claimed is:

1. A method of testing the flexibility of a pair of skis which have a camber at rest forming a gap when the skis are placed bottom to bottom, and which skis can be compressed toward each other when placed bottom to bottom to change the gap as a function of the force exerted on the pair of skis tending to compress them, said gap and said force forming parameters related to the flexibility of the skis, comprising the steps of compressing the bottom to bottom skis toward each other under a force applied and sensed adjacent the center portions of the skis, and monitoring at least one of the parameters as the skis are compressed until the one parameter is at a desired level and correlating the other parameter value with a skier's weight to determine the ski flexibility as a measure of suitability of use by the intended skier.

2. The method of claim 1 wherein the one parameter is force and the force is a desired proportion of the skier's weight, and the gap length is measured when the force is at a desired level.

3. The method of claim 1 wherein the one parameter is the gap and the gap is substantially eliminated, and the correlating comprises determining the closing force when the gap is substantially eliminated and comparing the closing force with the skier's weight.

4. A method for testing the flexibility of skis having camber causing a gap between a pair of skis placed bottom to bottom, and using a portable clamping member having a support, an adjustable member mounted on said clamping member movable to support said support, a force registering gage on the clamping member effective to measure force exerted by said movable member which is reacted into said support, said clamping member being of size to permit a pair of skis which are placed bottom to bottom to be received between the support and the movable member without initially substantially compressing the skis together in the region of greatest camber of said skis, comprising the steps of:

moving said adjustable member toward said support with the bottom to bottom skis between the support and adjustable member to compress said skis and to change the parameters which comprise gap between the skis and force registered on the force registering gage as the skis are compressed together, monitoring at least one of the parameters until that parameter is at a desired value and correlating the parameter values with an intended skier's weight to determine ski flexibility in relation to use by the intended skier.

5. The method of claim 4 wherein the skis are compressed together until the gap is substantially closed, and determining the force necessary to substantially close the gap for correlation to the intended skier's weight.

6. In combination with a pair of skis placed bottom to bottom with the normal camber creating a gap between the bottoms of the skis generally in the central portions of the skis, a device for measuring the ski stiffness, including a clamp member having a pair of legs which are spaced apart, a first of said legs supporting an adjustable member movable toward the other of said legs, and the other of said legs supporting a force measuring device, said force measuring device and said adjustable member being movable apart sufficiently to receive said skis, and said adjustable member being movable to compress said skis together at a measured force equal to a known proportion of the weight of a skier to use such skis, and means to determine the size of gap between the skis at the measured force.

7. The combination as specified in claim 6 wherein said adjustable means has sufficient adjustability to cause the bottom surfaces of said skis to be moved to position wherein they are contiguous adjacent the location of said clamp member.

8. A method of testing the flexibility of skis using a portable clamping member having a force registering gage at one location, and an adjustable member spaced from said force registering gage and movable toward said registering gage, said clamping member being of size to permit a pair of skis which are placed bottom to bottom to be received therebetween without compressing the skis in the area of the greatest camber of said skis comprising the steps of:

moving said adjustable member toward said force registering gage with the skis therebetween to compress said skis until the force registering member registers a force which is a desired proportion of the weight of the skier to use said skis, and determining the size of the gap remaining between the skis and the relationship of the gap to the location where the clamp is positioned on said skis.

9. The method as specified in claim 8 including placing said clamping member on said skis generally in the region where the ball of the foot of a skier would rest.

* * * * *